(12) United States Patent
Lee et al.

(10) Patent No.: US 10,287,441 B2
(45) Date of Patent: May 14, 2019

(54) COPOLYMER GRAFTED WITH OXAZOLINE BASED DERIVATIVE, COMPOSITION INCLUDING THE GRAFT COPOLYMER, AND ARTICLE INCLUDING THE COMPOSITION

(71) Applicant: Samsung Electronics Co., Ltd., Suwon-si, Gyeonggi-do (KR)

(72) Inventors: Moo Ho Lee, Suwon-si (KR); Won Cheol Jung, Seoul (KR); In Ki Kim, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 82 days.

(21) Appl. No.: 15/260,507

(22) Filed: Sep. 9, 2016

(65) Prior Publication Data
US 2017/0298233 A1    Oct. 19, 2017

(30) Foreign Application Priority Data
Apr. 14, 2016  (KR) .................. 10-2016-0045510

(51) Int. Cl.
| | |
|---|---|
| *C09D 5/16* | (2006.01) |
| *A01N 25/10* | (2006.01) |
| *A01N 25/34* | (2006.01) |
| *C09D 5/14* | (2006.01) |
| *C08F 255/02* | (2006.01) |
| *C08L 51/06* | (2006.01) |

(52) U.S. Cl.
CPC ............ *C09D 5/1637* (2013.01); *A01N 25/10* (2013.01); *A01N 25/34* (2013.01); *C08F 255/02* (2013.01); *C08L 51/06* (2013.01); *C09D 5/14* (2013.01); *C08F 2500/26* (2013.01); *C08L 2203/16* (2013.01)

(58) Field of Classification Search
None
See application file for complete search history.

(56) References Cited

U.S. PATENT DOCUMENTS

| | | | |
|---|---|---|---|
| 2009/0194479 | A1 | 8/2009 | Niu et al. |
| 2011/0123475 | A1 | 5/2011 | Dias et al. |
| 2011/0124772 | A1 | 5/2011 | Wang et al. |

FOREIGN PATENT DOCUMENTS

| | | |
|---|---|---|
| EP | 2223962 A1 | 9/2010 |
| JP | 2011140562 A | 7/2011 |
| WO | WO-2009126502 A2 | 10/2009 |
| WO | WO-2014095753 A1 | 6/2014 |

OTHER PUBLICATIONS

Weber Macromolecules 2013, 46, 5107-5116.*

* cited by examiner

*Primary Examiner* — Robert T Butcher
(74) *Attorney, Agent, or Firm* — Harness, Dickey & Pierce, P.L.C.

(57) ABSTRACT

A graft copolymer includes an oxazoline-based derivative grafted onto a polymer including a structural unit. A composition may include the copolymer, and an article may be manufactured from the composition.

19 Claims, 2 Drawing Sheets

COPOLYMER GRAFTED WITH OXAZOLINE BASED DERIVATIVE, COMPOSITION INCLUDING THE GRAFT COPOLYMER, AND ARTICLE INCLUDING THE COMPOSITION

CROSS REFERENCE TO RELATED APPLICATIONS

This application claims priority to and the benefit of Korean Patent Application No. 10-2016-0045510 filed in the Korean Intellectual Property Office on Apr. 14, 2016, the entire contents of which are incorporated herein by reference.

BACKGROUND

1. Field

A copolymer grafted with an oxazoline-based derivative, a composition including the copolymer, and an article manufactured from the composition are disclosed.

2. Description of the Related Art

Recently, the demand of antimicrobial and antifouling functionality in interior or exterior materials of electronic products including a laundry washing machine, a laundry drying machine, a refrigerator, an air conditioner, a mobile phone or the like has increased.

In some cases, a conventional technique for providing such antimicrobial and antifouling functionality includes providing a coating on an article surface, where the coating includes one or more antimicrobial and antifouling materials. However, because interior or exterior materials of home appliances are generally produced by extrusion or injection molding processes, additional antimicrobial and antifouling material coating processes after extrusion or injection molding of said appliances may result in an increase of processing cost. In terms of durability, adhesion of one or more coatings on a plastic surface, where the plastic surface is an interior or exterior material for a home appliance, may be insufficiently strong for home appliances requiring at least approximately long-term (e.g., 10 years) durability. Therefore, it may be desirable to develop antimicrobial and antifouling materials capable of being extruded and injection molded.

SUMMARY

Some example embodiments provide an antimicrobial and antifouling material which enables persistent antimicrobial and antifouling performance by at least partially mitigating leaching of antimicrobial and antifouling components from the material, and is compatible with polymer resins, such that the material may be extruded and injection molded; and an article produced therefrom.

In some example embodiments, a copolymer including an oxazoline-based derivative represented by Chemical Formula 1 grafted onto a polymer including a structural unit represented by Chemical Formula 2 is provided.

[Chemical Formula 1]

In Chemical Formula 1, $R^{11}$ is hydrogen or a methyl group, A is a substituted or unsubstituted $C_1$ to $C_{10}$ alkylene group, a substituted or unsubstituted $C_6$ to $C_{20}$ arylene group, or $-[C(=O)(CH_2)_m]_k-$, wherein m is an integer inclusively between 0 and 5 and k is an integer inclusively between 1 and 5. $R^{12}$ is a substituted or unsubstituted $C_1$ to $C_{10}$ alkyl group, a substituted or unsubstituted $C_3$ to $C_{20}$ cycloalkyl group, a substituted or unsubstituted $C_6$ to $C_{20}$ aryl group, or a substituted or unsubstituted $C_3$ to $C_{20}$ heterocyclic group, $R^1$ to $R^4$ are independently hydrogen, a halogen, hydroxy group, or a substituted or unsubstituted $C_1$ to $C_5$ alkyl group. "n" is an integer ranging from 3 to 300. $G^1$ to $G^3$ are independently a substituted or unsubstituted $C_1$ to $C_{30}$ alkyl group, a substituted or unsubstituted $C_3$ to $C_{20}$ cycloalkyl group, a substituted or unsubstituted $C_6$ to $C_{20}$ aryl group, or a substituted or unsubstituted $C_3$ to $C_{20}$ heterocyclic group, and $X^-$ is a halide ion, a hydroxide ion, a nitrate ion, a phosphate salt ion, a trifluoroacetate ion, or a sulfate ion.

[Chemical Formula 2]

In Chemical Formula 2, $R^{21}$ to $R^{24}$ are independently hydrogen, a substituted or unsubstituted $C_1$ to $C_{20}$ alkyl group, a substituted or unsubstituted $C_1$ to $C_{20}$ alkoxy group, a substituted or unsubstituted $C_3$ to $C_{20}$ cycloalkyl group, a substituted or unsubstituted $C_6$ to $C_{20}$ aryl group, a substituted or unsubstituted $C_3$ to $C_{20}$ heterocyclic group, a substituted or unsubstituted $C_2$ to $C_{20}$ ester group, a substituted or unsubstituted silyl group, a hydroxy group, a halogen, a nitrile group, a cyano group, or a combination thereof.

In Chemical Formula 1, $R^{12}$ may be a $C_1$ to $C_5$ alkyl group.

In Chemical Formula 1, at least one of $G^1$ to $G^3$ may be a $C_6$ to $C_{30}$ alkyl group.

In Chemical Formula 1, one of $G^1$ to $G^3$ may be a $C_6$ to $C_{30}$ alkyl group and each of a remainder of $G^1$ to $G^3$ may independently be a $C_1$ to $C_3$ alkyl group.

The oxazoline-based derivative represented by Chemical Formula 1 may be associated with a number average molecular weight that ranges from about 500 g/mol to about 30,000 g/mol.

The oxazoline-based derivative represented by Chemical Formula 1 that is included in the graft copolymer may be included in an amount of about 1 wt % to about 30 wt % based on the total weight of the graft copolymer.

In Chemical Formula 2, $R^{21}$ to $R^{24}$ may independently be hydrogen, or a substituted or unsubstituted $C_1$ to $C_{10}$ alkyl group.

The polymer including a structural unit represented by Chemical Formula 2 may be included in an amount of about 70 wt % to about 99 wt % based on the total weight of the graft copolymer.

In some example embodiments, a composition including the graft copolymer is provided.

The composition may further include an additional polymer that includes at least one of polyolefin, polyalkyl(meth)acrylate, polyacrylate, polyacrylonitrile, polystyrene, polyvinyl chloride, polyvinylidene chloride, polycarbonate, polyester, thermoplastic polyurethane, a silicone resin, polysulfone, polyamide, a rubber modified vinyl-based copolymer, and a copolymer thereof.

The additional polymer may further include the structural unit represented by Chemical Formula 2.

The additional polymer may be included in the composition in an amount of about 30 wt % to 99 wt % based on the total weight of the composition.

The oxazoline-based derivative represented by Chemical Formula 1 grafted onto the graft copolymer in the composition may be included, in the composition, in an amount of about 1 wt % to about 30 wt % based on the total weight of the composition.

The oxazoline-based derivative represented by Chemical Formula 1 grafted onto the graft copolymer in the composition may be included, in the composition, in an amount of about 1 wt % to about 20 wt % based on the total weight of the composition.

The composition may have greater than or equal to about 75% antibacterial rate for *Escherchia Coli*, which is measured by an antimicrobial test according to ISO 22196.

The composition may have greater than or equal to about 85% antibaterial rate for yellow *staphylococcus*, which is measured by an antimicrobial test according to ISO 22196.

In another embodiment, an article manufactured from the composition is provided.

The article may be manufactured based on at least one of extruding, coextruding, injection molding, and a double injection molding processes.

DETAILED DESCRIPTION

Example embodiments will hereinafter be described in detail, and may be easily performed by those who have common knowledge in the related art. However, this disclosure may be embodied in many different forms and is not construed as limited to the example embodiments set forth herein.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when a definition is not otherwise provided the term "substituted" refers to substitution with a substituent selected from a $C_1$ to $C_{30}$ alkyl group, a $C_2$ to $C_{30}$ alkynyl group, a $C_6$ to $C_{30}$ aryl group, a $C_7$ to $C_{30}$ alkylaryl group, a $C_1$ to $C_{30}$ alkoxy group, a $C_1$ to $C_{30}$ heteroalkyl group, a $C_3$ to $C_{30}$ heteroalkylaryl group, a $C_3$ to $C_{30}$ cycloalkyl group, a $C_3$ to $C_{15}$ cycloalkenyl group, a $C_6$ to $C_{30}$ cycloalkynyl group, a $C_2$ to $C_{30}$ heterocycloalkyl group, a halogen (F, Cl, Br, or I), a hydroxy group (—OH), a nitro group (—$NO_2$), a cyano group (—CN), and a combination thereof, instead of hydrogen of a compound.

As used herein, when a definition is not otherwise provided, the term "hetero" refers to one including 1 to 3 hetero atoms selected from N, O, S, Si, and P.

As used herein, the term "combination thereof" refers to a mixture, a stacked structure, a composite, a copolymer, an alloy, a blend, a reaction product of components.

In addition, "*" refers to a point of attachment to nitrogen or another atom.

In some example embodiments, a copolymer including an oxazoline-based derivative represented by Chemical Formula 1 grafted onto a polymer including a structural unit represented by Chemical Formula 2 is provided.

[Chemical Formula 1]

In Chemical Formula 1, $R^{11}$ is hydrogen or a methyl group, A is a substituted or unsubstituted $C_1$ to $C_{10}$ alkylene group, a substituted or unsubstituted $C_6$ to $C_{20}$ arylene group, or $—[C(=O)(CH_2)_m]_k—$, wherein m is an integer inclusively between 0 and 5 and k is an integer inclusively between 1 and 5, $R^{12}$ is a substituted or unsubstituted $C_1$ to $C_{10}$ alkyl group, a substituted or unsubstituted $C_3$ to $C_{20}$ cycloalkyl group, a substituted or unsubstituted $C_6$ to $C_{20}$ aryl group, or a substituted or unsubstituted $C_3$ to $C_{20}$ heterocyclic group, $R^1$ to $R^4$ are independently hydrogen, a halogen, a hydroxy group, or a substituted or unsubstituted $C_1$ to $C_5$ alkyl group, n is an integer ranging from 3 to 300, $G^1$ to $G^3$ are independently a substituted or unsubstituted $C_1$ to $C_{30}$ alkyl group, a substituted or unsubstituted $C_3$ to $C_{20}$ cycloalkyl group, a substituted or unsubstituted $C_6$ to $C_{20}$ aryl group, or a substituted or unsubstituted $C_3$ to $C_{20}$ heterocyclic group, and $X^-$ is a halide ion, a hydroxide ion, a nitrate ion, a phosphate salt ion, trifluoroacetate ion, or a sulfate ion.

[Chemical Formula 2]

In Chemical Formula 2, $R^{21}$ to $R^{24}$ are independently at least one of hydrogen, a substituted or unsubstituted $C_1$ to $C_{20}$ alkyl group, a substituted or unsubstituted $C_1$ to $C_{20}$ alkoxy group, a substituted or unsubstituted $C_3$ to $C_{20}$ cycloalkyl group, a substituted or unsubstituted $C_6$ to $C_{20}$ aryl group, a substituted or unsubstituted $C_3$ to $C_{20}$ heterocyclic group, a substituted or unsubstituted $C_2$ to $C_{20}$ ester group, a substituted or unsubstituted silyl group, a hydroxy group, a halogen, a nitrile group, and a cyano group.

In the graft copolymer, the polymer including a structural unit represented by Chemical Formula 2 may be a basic backbone and the oxazoline derivative represented by Chemical Formula 1 may be a side chain grafted onto the basic backbone.

The graft copolymer may have antimicrobial (antibacterial) functions. In particular, the graft copolymer may be configured to suppress bacterial propagation. The graft copolymer may have antifouling functions. In particular, the graft copolymer may be configured to prevent bacterial attachment. The graft copolymer may have good compatibility with a polymer resin and may be employed for an injection molding process.

It is well-known conventional antimicrobial technology to add a metal ion such as Ag, Cu, or Zn, or organometallic compound having one or more antimicrobial properties into a polymer resin. This releasing antimicrobial technology leaches out the metal ion or the organometallic compound slowly onto the surface of the polymer resin and thus imparts an antimicrobial function thereto. However, this technology has a problem of doing harm on a human body due to leaching of the antibacterial agent and not maintaining long-term antimicrobial performance and thus may not be appropriately applied to extruding and injection molding.

In addition, a conventional antifouling technology generally adopts coating using fluorine compound or a silicon compound. But, when applied to the extruding or injection molding process, the fluorine or silicon compound has a problem of insufficient compatibility with a polymer resin. In addition, silicone oil is reported to be used as an antifouling additive for the extruding process but has a problem of being leached out from a material when used for a long time and thus the durability of the material that includes the silicone oil may deteriorate over time.

The graft copolymer according to some example embodiments is a contact killing antimicrobial compound keeping an antimicrobial function without leaching an antimicrobial component and thus may realize long-term durability without leaching an antifouling component and also improve compatibility with a polymer resin.

Specifically, a quaternary ammonium group in the oxazoline-based derivative represented by Chemical Formula 1 may be configured to perform antimicrobial functionality in a contact killing method. The quaternary ammonium group is bonded with the graft copolymer and thus may not be leached out from a material that includes the graft copolymer but instead may configure the graft copolymer to provide antimicrobial functionality for the material for a long time.

In addition, in the oxazoline-based derivative represented by Chemical Formula 1, the oxazoline group may have hydrophilicity and be configured to provide antifouling functionality. The hydrophilic oxazoline group may reduce and/or prevent the attachment of pollutants to a material that includes the oxazoline-based derivative and may help enable easy removal of an attached pollutant from the material, when it is applied to interior materials of electronic products such as a washing machine, a refrigerator, and the like, where the interior materials are configured to be exposed to environments having a high relative humidity (e.g., >50% relative humidity).

Generally, hydrophilic polyoxazoline has problems of being not mixed with hydrophobic polymer resin. Accordingly, the conventional antifouling technologies using oxazoline-based derivatives such as a polyoxazoline, oxazoline oligomer, or an oxazoline copolymer mostly adopt coating process to avoid mixing oxazoline-based derivatives with hydrophobic polymer resin. Antimicrobial and antifouling coating can be applied on the surface of product which is manufactured by extrusion or injection molding process. But, the additional coating is not recommended due to the increase of cost and the deterioration of durability.

In some example embodiments, the graft copolymer has excellent compatibility with a polymer resin despite the hydrophilic oxazoline group and thus may be directly applied to extruding and injecting processes for forming a material of an appliance. For example, a C=C double bond (an unsaturated bond) in which $R^{11}$ is bonded in Chemical Formula 1 is a reactive group and thus may perform a graft polymerization reaction with a polymer including a structural unit represented by Chemical Formula 2. The graft copolymer may have improved compatibility with a polymer resin due to the polymer structural unit moiety represented by Chemical Formula 2. In addition, the graft copolymer structure may reduce and/or prevent an antimicrobial material or the antifouling material from leaching out of a material in which the graft copolymer structure is included and helps mixing with a polymer resin matrix, and so may be directly employed for an extrusion or injection molding process for forming a portion of an appliance.

In Chemical Formula 1, A may be, for example, a substituted or unsubstituted $C_1$ to $C_5$ alkylene group. A may be a methylene group or an ethylene group. A may be a substituted or unsubstituted $C_6$ to $C_{10}$ arylene group. A may be a phenylene group. A may be $—C(=O)—$, or $—C(=O)CH_2—$.

In Chemical Formula 1, $R^{12}$ may be, for example a substituted or unsubstituted $C_1$ to $C_5$ alkyl group. $R^{12}$ may be a methyl group, an ethyl group, or a propyl group, but is not limited thereto.

In Chemical Formula 1, n refers to a polymerization degree of an oxazoline structural unit, n is an integer ranging from 3 to 300. "n" may be 3 to 100. "n" may be 3 to 80. "n" may be 3 to 50. "n" may be 3 to 30. "n" may be 3 to 20. When n is within the range, the oxazoline-based derivative represented by Chemical Formula 1 may be configured to provide an improved antifouling functionality.

In Chemical Formula 1, $G^1$ to $G^3$ may be, for example, independently, a substituted or unsubstituted $C_1$ to $C_{20}$ alkyl group, a substituted or unsubstituted $C_5$ to $C_{10}$ cycloalkyl group, a substituted or unsubstituted $C_6$ to $Cm$ aryl group, or a substituted or unsubstituted $C_3$ to $Cm$ heterocyclic group.

In Chemical Formula 1, at least one of $G^1$ to $G^3$ may be a $C_6$ to $C_{30}$ alkyl group, that is an alkyl group having six or greater carbons. For example, at least one of $G^1$ to $G^3$ may be a $C_6$ to $C_{25}$ alkyl group, a $C_6$ to $C_{20}$ alkyl group, a $C_6$ to $C_{15}$ alkyl group, a $C_8$ to $C_{30}$ alkyl group, or a $C_{10}$ to $C_{30}$ alkyl group, but are not limited thereto. When at least one of $G^1$ to $G^3$ is an alkyl group having six or greater carbons, the quaternary ammonium group in Chemical Formula 1 may have an improved contact-killing antimicrobial functionality.

For example, one of $G^1$ to $G^3$ represented by Chemical Formula 1 may be a $C_6$ to $C_{20}$ alkyl group and the other two may independently be a $C_1$ to $C_3$ alkyl group. In this case, in Chemical Formula 1, the quaternary ammonium group may have more improved contact-killing antimicrobial functionality.

In Chemical Formula 1, $X^-$ is an anion that forms a salt with the quaternary ammonium cation. Non-limiting examples of $X^-$ may be $F^-$, $Cl^-$, $Br^-$, $I^-$, $OH^-$, $NO_3^-$, $H_2PO_4^-$, $CF_3COO^-$, $HSO_4^-$, and the like.

On the other hand, the oxazoline-based derivative represented by Chemical Formula 1 may be prepared by reacting an initiator represented by Chemical Formula 3, an oxazoline-based monomer represented by Chemical Formula 4, and a terminator represented by Chemical Formula 5.

[Chemical Formula 3]

In Chemical Formula 3, $R^{11}$ is hydrogen or a methyl group, A is a substituted or unsubstituted $C_1$ to $C_{10}$ alkylene group, a substituted or unsubstituted $C_6$ to $C_{20}$ arylene group, or $-[C(\!=\!O)(CH_2)_m]_k-$, wherein m is an integer inclusively between 0 and 5 and k is an integer inclusively between 1 and 5), and Z is F, Cl, Br, or I.

[Chemical Formula 4]

In Chemical Formula 4, $R^{12}$ is a substituted or unsubstituted $C_1$ to $C_{10}$ alkyl group, a substituted or unsubstituted $C_3$ to $C_{20}$ cycloalkyl group, a substituted or unsubstituted $C_6$ to $C_{20}$ aryl group, or a substituted or unsubstituted $C_3$ to $C_{20}$ heterocyclic group, $R^1$ to $R^4$ are independently hydrogen, a halogen, a hydroxy group, or a substituted or unsubstituted $C_1$ to $C_5$ alkyl group.

[Chemical Formula 5]

In Chemical Formula 5, $G^1$ to $G^3$ are independently a substituted or unsubstituted $C_1$ to $C_{30}$ alkyl group, a substituted or unsubstituted $C_3$ to $C_{20}$ cycloalkyl group, a substituted or unsubstituted $C_6$ to $C_{20}$ aryl group, or a substituted or unsubstituted $C_3$ to $C_{20}$ heterocyclic group.

The oxazoline-based derivative represented by Chemical Formula 1 may be produced by mixing the initiator represented by Chemical Formula 3 and the oxazoline-based monomer represented by Chemical Formula 4; polymerizing the same at about 40° C. to about 120° C. for about 1 hour to about 20 hours; subsequently, adding the terminator represented by Chemical Formula 5 and reacting the same at about 40° C. to about 120° C. for about 1 hour to about 24 hours; and then by purifying and drying the resultant product.

The initiator represented by Chemical Formula 3 may be, for example, acryloyl halide, or methacryloyl halide, but is not limited thereto. The halide may be fluoride, chloride, bromide, or iodide, but is not limited thereto. When the initiator is an allyl halide, $R^{11}$ is hydrogen and A is $-CH_2-$. When the initiator is an acryloyl halide, $R^{11}$ is hydrogen and A is $-C(\!=\!O)-$ and when it is a methacryloyl halide, $R^{11}$ is a methyl group and A is $-C(\!=\!O)-$.

The oxazoline-based monomer represented by Chemical Formula 4 may be, for example, 2-methyl-2-oxazoline, 2-ethyl-2-oxazoline, or 2-propyl-2-oxazoline, but is not limited thereto.

During the synthesis of the oxazoline-based derivative represented by Chemical Formula 1, a polymerization degree of the oxazoline-based monomer may be about 3 to about 300, for example, about 5 to about 100, about 5 to about 50, or about 10 to about 30. In this case, the oxazoline-based derivative represented by Chemical Formula 1 may have improved antifouling functionality.

A number average molecular weight of the oxazoline-based derivative represented by Chemical Formula 1 may be about 500 g/mol to about 30,000 g/mol, for example, about 1,000 g/mol to about 9,000 g/mol, or about 3,000 g/mol to about 8,000 g/mol. In this case, the oxazoline-based derivative represented by Chemical Formula 1 may have improved antimicrobial and antifouling functionality.

The oxazoline-based derivative represented by Chemical Formula 1 may be included in a graft copolymer in an amount of about 1 wt % to about 30 wt % based on the total weight of the graft copolymer. The oxazoline-based derivative represented by Chemical Formula 1 may be included in a graft copolymer in an amount of about 1 wt % to about 25 wt % based on the total weight of the graft copolymer. The oxazoline-based derivative represented by Chemical Formula 1 may be included in a graft copolymer in an amount of about 1 wt % to about 15 wt % based on the total weight of the graft copolymer. The oxazoline-based derivative represented by Chemical Formula 1 may be included in a graft copolymer in an amount of about 1 wt % to about 10 wt % based on the total weight of the graft copolymer. The oxazoline-based derivative represented by Chemical Formula 1 may be included in a graft copolymer in an amount of about 1 wt % to about 5 wt % based on the total weight of the graft copolymer. In some example embodiments, a graft copolymer that includes the oxazoline-based derivative may be configured to maintain improved antimicrobial/antifouling functionality continuously and have good compatibility with a polymer resin.

The polymer including a structural unit represented by Chemical Formula 2 may be, for example, polyolefin, polyalkyl(meth)acrylate, polyacrylate, polystyrene, polyvinyl chloride, polyvinylidene chloride, or a copolymer thereof. The polymer including a structural unit represented by Chemical Formula 2 may make the graft copolymer mix with a polymer resin matrix.

For example, in Chemical Formula 2, $R^{21}$ to $R^{24}$ may independently be hydrogen, or a substituted or unsubstituted $C_1$ to $C_{10}$ alkyl group. That is, the polymer including a structural unit represented by Chemical Formula 2 may be polyolefin, for example polyethylene, polypropylene, polybutylene, and the like.

The polymer including a structural unit represented by Chemical Formula 2 may be included in a graft copolymer in an amount of about 70 wt % to about 99 wt % based on the total weight of the graft copolymer. The polymer including a structural unit represented by Chemical Formula 2 may be included in a graft copolymer in an amount of about 75 wt % to about 99 wt % based on the total weight of the graft copolymer. The polymer including a structural unit represented by Chemical Formula 2 may be included in a graft copolymer in an amount of about 80 wt % to about 99 wt % based on the total weight of the graft copolymer. The polymer including a structural unit represented by Chemical Formula 2 may be included in a graft copolymer in an amount of about 90 wt % to about 99 wt % based on the total weight of the graft copolymer.

When the polymer including a structural unit represented by Chemical Formula 2 is included within the ranges, the graft copolymer has improved compatibility with a polymer resin and realizes improved antimicrobial/antifouling functionality simultaneously.

The graft copolymer may be easily prepared by a graft-copolymerization using the oxazoline-based derivative represented by Chemical Formula 1 and the polymer including a structural unit represented by Chemical Formula 2 and a peroxide initiator.

Specifically, the peroxide as a radical-forming initiator may generate a radical at a carbon atom represented by Chemical Formula 2 and bring about a graft-copolymerization with a C=C double bond represented by Chemical Formula 1. The peroxide initiator may be, for example, a $C_3$ to $C_{30}$ organic peroxide, for example, a dialkyl peroxide, a diacyl peroxide, a hydroperoxide, a ketone peroxide, a peroxy ketal, a peroxy ester, a peroxy carbonate, and the like.

Specific examples of the peroxide may be benzoyl peroxide, m-toluoyl peroxide, dicumyl peroxide, t-butyl peroxide, isobutyl peroxide, 3,5,5-trimethylhexanoyl peroxide, methyl ethyl ketone peroxide, lauroyl peroxide, stearoyl peroxide, succinyl peroxide, t-butyl peroxy-2-ethylhexanoate, t-butyl peroxyneodecanoate, t-butyl peroxybenzoate, t-butyl peroxypivalate, t-butylperoxy isopropyl carbonate, diisopropyl peroxydicarbonate, bis-(4-t-butylcyclohexyl) peroxydicarbonate, dicyclohexyl peroxydicarbonate, but are not limited thereto.

The peroxide may be used in an amount of about 0.01 parts by weight to about 5 parts by weight, for example, about 0.01 parts by weight to about 4 parts by weight, for example, about 0.1 parts by weight to about 5 parts by weight based on 100 parts by weight of the polymer including a structural unit represented by Chemical Formula 2. When the peroxide initiator is used within the ranges, graft-copolymerization reaction may smoothly be performed.

The oxazoline-based derivative represented by Chemical Formula 1 may be used in an amount of about 1 wt % to about 30 wt %, for example, about 1 wt % to about 25 wt %, about 1 wt % to about 20 wt %, about 1 wt % to about 10 wt %, about 1 wt % to about 5 wt % based on the total amount of the oxazoline-based derivative represented by Chemical Formula 1 and the polymer including a structural unit represented by Chemical Formula 2. In this case, the graft copolymer may maintain improved antimicrobial/antifouling functionality continuously and have good compatibility with a polymer resin.

In the graft-copolymerization process, the polymer including a structural unit represented by Chemical Formula 2 may be used in an amount of about 70 wt % to about 99 wt %, for example, about 75 wt % to about 99 wt %, about 80 wt % to about 99 wt %, about 90 wt % to about 99 wt %, or about 95 wt % to about 99 wt % based on the total amount of the oxazoline-based derivative represented by Chemical Formula 1 and the polymer including a structural unit represented by Chemical Formula 2. In this case, the graft copolymer may have good compatibility with a polymer resin and maintain improved antimicrobial/antifouling functionality continuously.

The graft-copolymerization process may be performed in a reactive blending (or reactive melt blending) method by using a twin-screw extruder. In other words, the oxazoline-based derivative represented by Chemical Formula 1, a polymer including the structural unit represented by Chemical Formula 2, and peroxide as a radical-generating initiator are fed into an extruder without any pretreatment synthesis process and then, grafting reaction take place during extrusion process and graft copolymer is extruded as a pellet. Accordingly, the graft copolymer may be simply and economically manufactured.

The reactive blending process for manufacturing the graft copolymer may be performed within a range of about 150° C. to about 300° C.

In another embodiment, a composition including the graft copolymer is provided.

As described above, the graft copolymer may have antimicrobial and antifouling functionality due to the oxazoline-based compound represented by Chemical Formula 1, and may provide a resin composition including the structural unit represented by Chemical Formula 2 grafted with the compound represented by Chemical Formula 1.

Accordingly, the resin composition is used alone or mixed with an additional polymer and thus may be applied to extruding, injection molding, or the like.

When the composition further includes the additional polymer, the graft copolymer in the composition may play a role of a kind of additive having an antimicrobial and antifouling functionality. The graft copolymer has improved compatibility with the additional polymer and may impart a long-term effect of antimicrobial and antifouling. As the antimicrobial material or the antifouling material is not leached out the composition has a continuous antimicrobial and antifouling functionality and improved durability required for extrusion or injection molding process. The composition is suitable to be employed for home appliances such as a washing tub of washing machine, an interior material of refrigerator, an external or internal material of air conditioner, and a dust bag of cleaning machine, which requires antimicrobial and antifouling functionality and durability.

The composition according to some example embodiments may be a composite including the graft copolymer and the additional polymer. The graft copolymer may be dispersed in the additional polymer, and in this case, the graft copolymer may be a kind of additive and the additional polymer may be a kind of matrix resin.

The additional polymer is not particularly limited as long as the generally used matrix resin. For example, the polymer may be a polymer including the structural unit represented by Chemical Formula 2. For example, the polymer may be polyolefin, polyalkyl(meth)acrylate, polyacrylate, polyacrylonitrile, polystyrene, polyvinyl chloride, polyvinylidene chloride, polycarbonate, polyester, thermoplastic polyurethane, a silicone resin, polysulfone, polyamide, a rubber modified vinyl-based copolymer, a copolymer thereof, or a combination thereof. Herein, the polymer has good compatibility with the graft copolymer.

The polyolefin may be a resin of polyethylene, polypropylene, or a copolymer thereof. The alkyl(meth)acrylate has a substituted or unsubstituted $C_1$ to $C_{10}$ alkyl group, methyl (meth)acrylate, ethyl(meth)acrylate, butyl(meth)acrylate, glycidyl(meth)acrylate, hydroxyethyl(meth)acrylate, and the like. The polycarbonate may be prepared by reacting diphenol with a phosgene, a halogen formate, a carbonate ester, or a combination thereof, and may be a linear polycarbonate, a branched polycarbonate, a polyestercarbonate copolymer, and the like.

The polyester may be a non-crystalline polyester resin modified by mixing for example polyethylene terephthalate, polytrimethylene terephthalate, polybutylene terephthalate, polyhexamethylene terephthalate, polycyclohexane dimethylene terephthalate, or resins thereof, with other monomers.

The rubber modified vinyl-based copolymer resin may include a rubbery polymer and a vinyl-based polymer and the rubbery polymer may be, for example a butadiene rubber, an acrylic rubber, an ethylene/propylene rubber, a styrene/butadiene rubber, an acrylonitrile/butadiene rubber, an isoprene rubber, or a combination thereof. In addition, the vinyl-based polymer may be a polymer of a first vinyl-based monomer, for example an aromatic vinyl monomer, an acryl-based monomer, a hetero cyclic monomer, or a combination thereof and a second vinyl-based monomer of an unsaturated nitrile monomer, an acryl-based monomer, a hetero cyclic monomer, or a combination thereof. The rubber modified vinyl-based copolymer may be a copolymer wherein styrene, acrylonitrile and/or methyl(meth)acrylate that is graft-copolymerized onto a butadiene rubber, an acrylic rubber, or a styrene/butadiene rubber, for example an acrylonitrile-butadiene-styrene resin.

The polymer may be, for example, the same material as the polymer including a structural unit represented by Chemical Formula 2. In this case, compatibility between the polymer and the graft copolymer may be improved.

In the composition, the polymer may be included in an amount of about 30 wt % to about 99 wt % based on the total weight of the composition. In the composition, the polymer may be included in an amount of about 40 wt % to about 99 wt % based on the total weight of the composition. In the composition, the polymer may be included in an amount of about 50 wt % to about 99 wt % based on the total weight of the composition. In the composition, the polymer may be included in an amount of about 60 wt % to about 99 wt % based on the total weight of the composition. When the polymer is included within the ranges, the composition may be desirable for interior or exterior material of home appliances requiring antimicrobial antifouling functionality.

The oxazoline-based derivative represented by Chemical Formula 1 grafted onto the graft copolymer may be included in an amount of about 1 wt % to about 30 wt % based on the total weight of the composition. The oxazoline-based derivative represented by Chemical Formula 1 grafted onto the graft copolymer may be included in an amount of about 1 wt % to about 25 wt % based on the total weight of the composition. The oxazoline-based derivative represented by Chemical Formula 1 grafted onto the graft copolymer may be included in an amount of about 1 wt % to about 20 wt % based on the total weight of the composition. The oxazoline-based derivative represented by Chemical Formula 1 grafted onto the graft copolymer may be included in an amount of about 2 wt % to about 30 wt % based on the total weight of the composition. The oxazoline-based derivative represented by Chemical Formula 1 grafted onto the graft copolymer may be included in an amount of about 1 wt % to about 15 wt % based on the total weight of the composition. The oxazoline-based derivative represented by Chemical Formula 1 grafted onto the graft copolymer may be included in an amount of about 1 wt % to about 10 wt % based on the total weight of the composition. The oxazoline-based derivative represented by Chemical Formula 1 grafted onto the graft copolymer may be included in an amount of about 2 wt % to about 15 wt % based on the total weight of the composition. The oxazoline-based derivative represented by Chemical Formula 1 grafted onto the graft copolymer may be included in an amount of about 2 wt % to about 10 wt % based on the total weight of the composition. The oxazoline-based derivative represented by Chemical Formula 1 grafted onto the graft copolymer may be included in an amount of about 2 wt % to about 5 wt % based on the total weight of the composition. When the graft copolymer is included within the ranges, the composition may be desirable for interior or exterior material of home appliances requiring antimicrobial antifouling functionality.

In another embodiment, an article formed from the composition including the graft copolymer is provided.

As described above, the graft copolymer may be applied alone or with an additional polymer having sufficient compatibility with the graft copolymer to manufacture an article having antimicrobial and antifouling performance by extrusion or injection molding process.

Unlike the conventional antimicrobial and/or antifouling coating, a resin itself forming the article includes the grafted oxazoline-based compound represented by Chemical Formula 1 as the antimicrobial and antifouling component, so the article does not cause problems of the harmfulness to the human body due to the leaching of antimicrobial and antifouling component. In addition, it may stably provide a long-term durability of antimicrobial and antifouling functionality.

Also the article is manufactured by the simple method.

Like the method of preparing the graft copolymer, the resin composition may be prepared by co-extrusion of the graft copolymer and additional polymer, and then injection molded into article. The method is clear and easily conscious by a person having the ordinary skills in the art, so it may easily product the molded article having the antimicrobial/antifouling functionality according to the embodiment using the method.

EXAMPLES

Hereinafter, the present disclosure is illustrated in more detail with reference to examples and comparative examples. However, the following examples and comparative examples are provided for the purpose of descriptions and the present disclosure is not limited thereto.

Synthesis Example 1

Synthesis of Oxazoline-based Derivative

A polymerization reaction is conducted at 80° C. under a normal pressure for 12 hours using allyl bromide as an initiator, methyl oxazoline as an oxazoline-based monomer, and acetonitrile as a solvent. Subsequently, dimethyldodecylamine as a terminator is added thereto under a chloroform solvent, and the mixture is reacted at 80° C. for 12 hours. A polymerized compound is precipitated using diethyl ether and then, filtered and dried. A ratio of the allyl bromide and the methyl oxazoline is adjusted to obtain an oxazoline-based derivative with a polymerization degree of 5 to 50 such as Chemical Formula 6. Polymerization yield is 80 weight % to 90 weight %.

[Chemical Formula 6]

In Chemical Formula 6, n is 5 to 50.

Example 1

Preparation of Graft Copolymer

A oxazoline-based derivative grafted polypropylene copolymer is obtained by a reactive melt blending of 5 to 30 wt. % of the oxazoline-based derivative represented by Chemical Formula 6 according to Synthesis Example 1, 70 to 95 wt. % of polypropylene, and 0.1 parts by weight or 0.5 parts by weight of dicumyl peroxide (DCP) or 0.1 parts by weight or 5.0 parts by weight of benzoyl peroxide (BPO) based on 100 parts by weight of the polypropylene.

The twin-screw extruder is set to have a temperature profile of 170° C., 200° C., 200° C., 200° C., 200° C., 185° C., and 175° C. and a rotation speed of 40 rpm to 80 rpm for the reactive melt blending.

The grafted copolymer obtained in the reactive melt blending method is a pellet having a size of about 0.5 mm to 2 mm.

Preparation Examples 1 to 6 and Comparative Examples 1 to 2

Manufacture of Injection Specimens

The pellets according to Examples are used to obtain each injection molded specimen according to Preparation Examples 1 to 6 and Comparative Examples 1 to 2.

Herein, the content of the oxazoline-based derivative represented by Chemical Formula 6 and a kind and content of an initiator used in each Preparation Example are provided in Table 1.

In Comparative Examples, each pellet is obtained according to the same reactive melt blending method as Example 1 by injecting polypropylene and the oxazoline-based derivative represented by Chemical Formula 6 except for DCP or BPO as a radical initiator into a twin-screw extruder. The contents of the polypropylene and the oxazoline-based derivative used in each Comparative Example are shown in Table 1.

During the injection molding, a melting temperature is set at 220° C., a mold temperature is set at 30° C., and an injection pressure is set at 750 bars. The specimens have a size of 62 mm (length)×12 mm (width)×3 mm (thickness).

TABLE 1

|  | Polypropylene (wt. %) | Oxazoline-based derivative (wt. %) | Radical initiator (part by weight) |
|---|---|---|---|
| Preparation Example 1 | 70 | 30 | DCP 0.5 |
| Preparation Example 2 | 90 | 10 | DCP 0.25 |
| Preparation Example 3 | 90 | 10 | BPO 0.5 |
| Preparation Example 4 | 95 | 5 | BPO 0.35 |
| Comparative Example 1 | 70 | 30 | — |
| Comparative Example 2 | 90 | 10 | — |
| Control | 100 | — | — |

Evaluation Example 1

Confirmation of Grafting

A thermo gravimetric analysis (TGA) is performed to examine if the oxazoline-based derivative is grafted onto polypropylene, and the results are shown in Table 2. In the TGA analysis, Comparative Example 1 shows an oxazoline-based derivative peak ratio of 26.0%, but Preparation Example 1 shows that the oxazoline-based derivative peak ratio is decreased into 11.4%, since the polypropylene is grafted with the oxazoline-based derivative. Accordingly, grafting of the oxazoline-based derivative onto the polypropylene is confirmed.

TABLE 2

|  | Polypropylene (wt. %) | Oxazoline-based derivative (wt. %) | Radical initiator (part by weight) | Oxazoline-based derivative peak ratio (%) |
|---|---|---|---|---|
| Preparation Example 1 | 70 | 30 | DCP 0.5 | 11.4 |
| Comparative Example 1 | 70 | 30 | — | 26.0 |

Evaluation Example 2

Compatibility of Graft Copolymer

Figure 1:
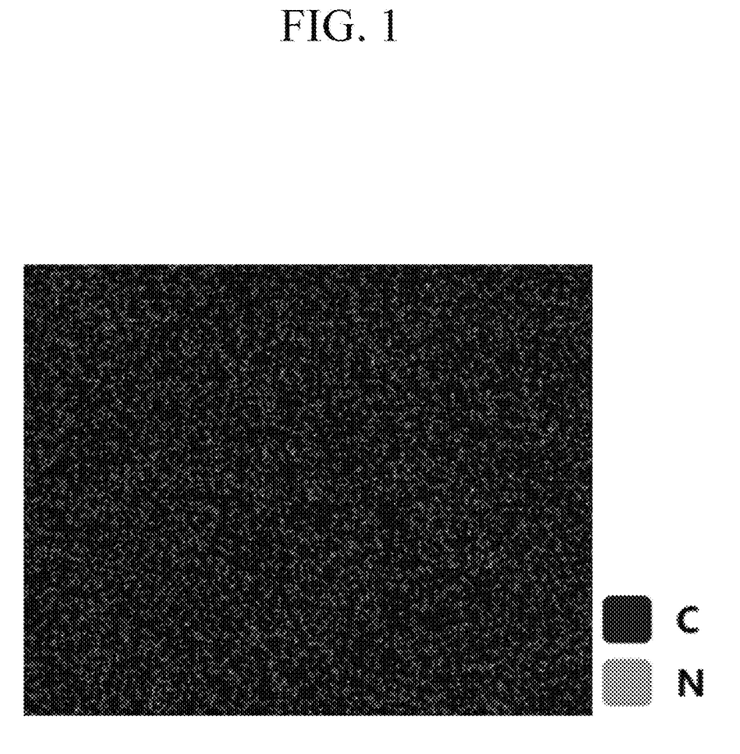
FIG. 1 is a scanning electron microscope (SEM) photograph showing the surface of the molded specimen according to some example embodiments.
Figure 2:
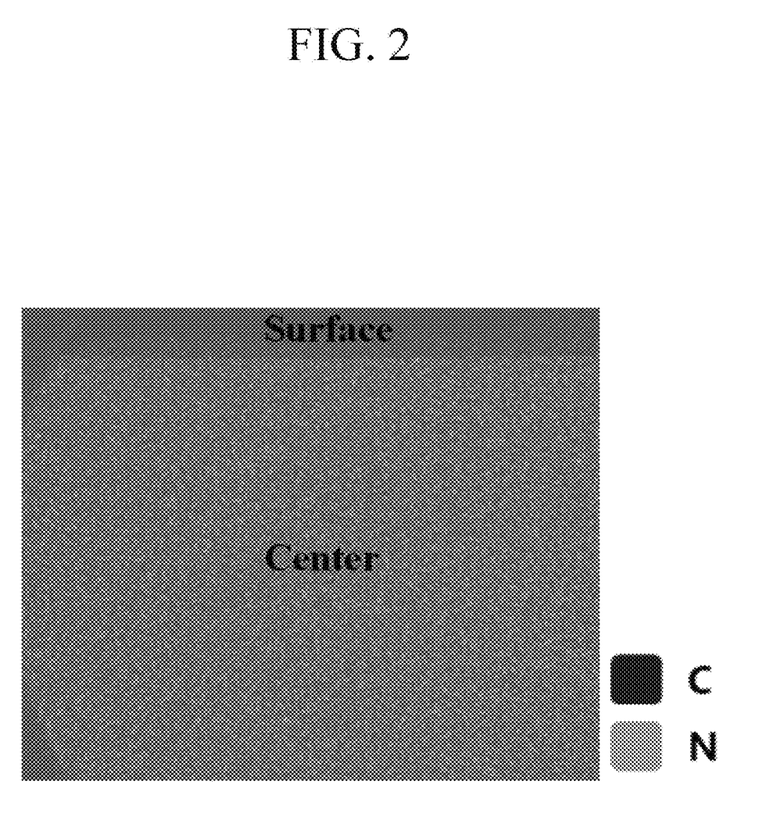
FIG. 2 is a scanning electron microscope (SEM) photograph showing the cross-section of the molded specimen according to some example embodiments.

The injection molded specimen according to Preparation Example 2 is element-mapping analyzed by using a scanning electron microscope (SEM) photograph. An element mapping about the surface of the injection molded specimen is shown in FIG. 1, and another element mapping about the cross section of the injection molded specimen is shown in FIG. 2. Referring to FIGS. 1 and 2, the nitrogen which is the element of the oxazoline is uniformly dispersed in the injection molded specimen. Accordingly, the oxazoline-based derivative turns out to be uniformly dispersed in the injection molded specimen.

Evaluation Example 3

Antimicrobial Evaluation

The injection molded specimens according to Preparation Examples 2 to 4 and Comparative Example 2 are used to measure an antimicrobial rate for yellow *staphylococcus* and *E. coli* according to ISO 22196 which is an antimicrobial measuring method of a plastic surface, and the results are shown in Table 3.

A high-temperature water test is performed by examining if the antimicrobial performance is deteriorated or not to evaluate a long-term stability of the antimicrobial performance under a severe condition of dipping each specimen in a 90° C. water bath for 16 hours.

Preparation Example 2 of the oxazoline-based compound grafted polypropylene using DCP as a radical initiator shows excellent antimicrobial performance and almost same antimicrobial rate even after the high-temperature water test.

On the contrary, Comparative Example 2 in which initiator is not used and oxazoline-based compound does not be grafted with polypropylene shows a sharply deteriorated antimicrobial rate since the oxazoline-based compound is leached out during the high-temperature water test.

measured and compared with the mass change of a neat polypropylene specimen as a control group before and after dipping in the artificial washing water to obtain an antifouling rate according to the following equation, and the results are shown in Table 4.

Antifouling rate (%)=(mass change of polypropylene−mass change of antifouling specimen)/ (mass change of polypropylene)×100

The specimens according to Preparation Examples 2 and 3 show 30-40% improved antifouling rate compared with the polypropylene as a control group and maintains the antifouling degree after the high-temperature water precipitation test.

On the contrary, Comparative Example 2 in which polypropylene is not grafted with the oxazoline-based compound using no initiator shows sharply deteriorated antifouling performance since the oxazoline-based compound having antifouling characteristics is leaching out during the high-temperature water leaching test.

The antifouling characteristics of the oxazoline-based compound come from the hydrophilicity of oxazoline chain structure, and the hydrophilicity is examined by measuring a water contact angle of each specimen. Preparation Examples 2 and 3 show 85-90 degrees of water contact angle decreased by the oxazoline-based compound, whereas 93.5 degrees of a water contact angle of the polypropylene.

TABLE 3

| | Specimen composition | | Antimicrobial rate before high-temperature water test (%) | | Antimicrobial rate after high-temperature water test (%) | |
|---|---|---|---|---|---|---|
| | oxazoline-based compound (mass %) | initiator (part by mass) | *E. coli* | *staphylococcus* | *E. coli* | *staphylococcus* |
| Preparation Example 2 | 10% | DCP 0.25 | 93.1 | 99.5 | 82.6 | 98.4 |
| Preparation Example 3 | 10% | BPO 0.5 | 88.4 | 99.2 | 24.9 | 93.6 |
| Preparation Example 4 | 5% | BPO 0.35 | 41.5 | 98.0 | 36.3 | 97.5 |
| Comparative Example 2 | 10% | — | 61.5 | 92.6 | 25.8 | 34.7 |

Evaluation Example 4

Antifouling Evaluation

An antifouling rate is evaluated using artificially prepared washing water for a washer, and the washing water has a composition of a liquid detergent of 0.9 mass %, a dust (JIS Test Powder1-class8) of 0.04 mass %, and a second-cut cotton linter of 0.8 mass %.

Each specimen is three times repetitively dipped in the artificial wash water for one minute while the washing water is stirred and then, taken out and dried. After drying, the mass change of the specimen before and after the dipping is

TABLE 4

| | Composition | | Before high-temperature water test | | After high-temperature water test | |
|---|---|---|---|---|---|---|
| | oxazoline-based compound (mass %) | initiator (part by mass) | anti-fouling rate (%) | water contact angle (°) | anti fouling rate (%) | water contact angle (°) |
| Preparation Example 2 | 10 | DCP 0.25 | 35.9 | 89.0 | 37.2 | 89.0 |
| Preparation Example 3 | 10 | BPO 0.5 | 39.1 | 85.7 | 35.3 | 88.3 |
| Comparative Example 2 | 10 | — | 39.1 | 88.9 | −9.6 | 93.0 |
| control | PP 100% | | 0.0 | 93.5 | — | — |

While this disclosure has been described in connection with what is presently considered to be practical example embodiments, it is to be understood that the example embodiments are not limited to the disclosed example embodiments, but, on the contrary, is intended to cover various modifications and equivalent arrangements included within the spirit and scope of the appended claims.

What is claimed is:

1. A graft copolymer comprising:
a copolymer including an oxazoline-based derivative grafted onto a polymer, the oxazoline-based derivative represented by Chemical Formula 1, the polymer including a structural unit represented by Chemical Formula 2:

[Chemical Formula 1]

wherein, in Chemical Formula 1,
$R^{11}$ is hydrogen or a methyl group,
A is
an unsubstituted $C_1$ to $C_{10}$ alkylene group,
$R^{12}$ is
a substituted or unsubstituted $C_1$ to $C_{10}$ alkyl group,
a substituted or unsubstituted $C_3$ to $C_{20}$ cycloalkyl group,
a substituted or unsubstituted $C_6$ to $C_{20}$ aryl group, or
a substituted or unsubstituted $C_3$ to $C_{20}$ heterocyclic group,
$R^1$ to $R^4$ are independently
hydrogen,
a halogen,
a hydroxy group, or
a substituted or unsubstituted $C_1$ to $C_5$ alkyl group,
n is an integer inclusively between 3 and 300,
$G^1$ to $G^3$ are independently
a substituted or unsubstituted $C_1$ to $C_{30}$ alkyl group,
a substituted or unsubstituted $C_3$ to $C_{20}$ cycloalkyl group,
a substituted or unsubstituted $C_6$ to $C_{20}$ aryl group, or
a substituted or unsubstituted $C_3$ to $C_{20}$ heterocyclic group, and
$X^-$ is
a halide ion,
a hydroxide ion,
a nitrate ion,
a phosphate salt ion,
a trifluoroacetate ion, or
a sulfate ion,

[Chemical Formula 2]

wherein, in Chemical Formula 2,
$R^{21}$ to $R^{24}$ are independently at least one of
hydrogen,
a substituted or unsubstituted $C_1$ to $C_{20}$ alkyl group,
a substituted or unsubstituted $C_1$ to $C_{20}$ alkoxy group,
a substituted or unsubstituted $C_3$ to $C_{20}$ cycloalkyl group,
a substituted or unsubstituted $C_6$ to $C_{20}$ aryl group,
a substituted or unsubstituted $C_3$ to $C_{20}$ heterocyclic group,
a substituted or unsubstituted $C_2$ to $C_{20}$ ester group,
a substituted or unsubstituted silyl group,
a hydroxy group,
a halogen,
a nitrile group, and
a cyano group.

2. The graft copolymer of claim 1, wherein $R^{12}$ represented by Chemical Formula 1 is a $C_1$ to $C_5$ alkyl group.

3. The graft copolymer of claim 1, wherein at least one of $G^1$ to $G^3$ is a $C_6$ to $C_{30}$ alkyl group.

4. The graft copolymer of claim 1, wherein one of $G^1$ to $G^3$ is a $C_6$ to $C_{30}$ alkyl group and each of a remainder of $G^1$ to $G^3$ are independently a $C_1$ to $C_3$ alkyl group.

5. The graft copolymer of claim 1, wherein the oxazoline-based derivative represented by Chemical Formula 1 is associated with a number average molecular weight that ranges from about 500 g/mol to about 30,000 g/mol.

6. The graft copolymer of claim 1, wherein the oxazoline-based derivative represented by Chemical Formula 1 that is included in the graft copolymer is included in an amount of about 1 wt % to about 30 wt % based on the total weight of the graft copolymer.

7. The graft copolymer of claim 1, wherein $R^{21}$ to $R^{24}$ represented by Chemical Formula 2 are independently
hydrogen, or
a substituted or unsubstituted $C_1$ to $C_{10}$ alkyl group.

8. The graft copolymer of claim 1, wherein the polymer including a structural unit represented by Chemical Formula 2 that is included in the graft copolymer is included in an amount of about 70 wt % to about 99 wt % based on the total weight of the graft copolymer.

9. A composition including the graft copolymer of claim 1.

10. The composition of claim 9, wherein the composition is a composition including the graft copolymer and further including an additional polymer, the additional polymer including at least one of
polyolefin,
polyalkyl(meth) acrylate,
polyacrylate,
polyacrylonitrile,
polystyrene,
polyvinyl chloride,
polyvinylidene chloride,
polycarbonate,
polyester,
thermoplastic polyurethane,
a silicone resin,
polysulfone,
polyamide,
a rubber modified vinyl-based copolymer, and
a copolymer thereof.

11. The composition of claim 10, wherein the additional polymer further includes the structural unit represented by Chemical Formula 2.

12. The composition of claim 10, wherein the additional polymer is included in the composition in an amount of about 30 wt % to 99 wt % based on the total weight of the composition.

13. The composition of claim 9, wherein the oxazoline-based derivative, represented by Chemical Formula 1, that is grafted onto the graft copolymer in the composition is included, in the composition, in an amount of about 1 wt % to about 30 wt % based on the total weight of the composition.

14. The composition of claim 9, wherein the oxazoline-based derivative, represented by Chemical Formula 1, that is grafted onto the graft copolymer in the composition is included, in the composition, in an amount of about 1 wt % to about 20 wt % based on the total weight of the composition.

15. The composition of claim 9, wherein the composition has a greater than or equal to about 75% antimicrobial rate for Escherichia Coli, which is measured by an antimicrobial test according to ISO 22196.

16. The composition of claim 9, wherein the composition has a greater than or equal to about 85% antibacterial rate for yellow staphylococcus, which is measured by an antimicrobial test according to ISO 22196.

17. An article manufactured from the composition of claim 9.

18. The article of claim 17, wherein the article is manufactured based on at least one of
   extrusion,
   co-extrusion,
   injection molding, and
   a double injection molding processes.

19. The graft copolymer according to claim 1, wherein the graft copolymer is prepared by a graft-copolymerization using the oxazoline-based derivative represented by Chemical Formula 1 and the polymer including a structural unit represented by Chemical Formula 2 and a peroxide initiator, wherein the peroxide initiator is included in an amount of 0.1 parts by weight to 5 parts by weight based on 100 parts by weight of the polymer.

* * * * *